US005705336A

United States Patent [19]
Reed et al.

[11] Patent Number: 5,705,336
[45] Date of Patent: Jan. 6, 1998

[54] ASSAY FOR SENSITIVITY OF TUMORS TO DNA-PLATINATING CHEMOTHERAPY

[75] Inventors: Eddie Reed, Germantown; Meenakshi Dabholkar, Bethesda, both of Md.

[73] Assignee: The United States of America as represented by the Department of Health and Human Services, Washington, D.C.

[21] Appl. No.: 399,617

[22] Filed: Mar. 7, 1995

[51] Int. Cl.$^6$ .............. C12Q 1/68; C07H 21/04; C12P 19/34

[52] U.S. Cl. .......... 435/6; 435/91.2; 435/91.21; 435/91.5; 435/91.51; 436/63; 436/64; 536/24.31; 536/24.33; 935/77; 935/78

[58] Field of Search .......... 435/6, 91.2, 91.21, 435/91.5, 91.51; 436/64, 63; 536/24.31, 24.33; 935/77, 78

[56] References Cited

U.S. PATENT DOCUMENTS 5,085,983  2/1992  Scanlon .................... 435/6

OTHER PUBLICATIONS

Kelland, European Journal of Cancer (Jun. 1994) 30A:725–727.
Dabholkar et al., Oncology Reports 2:209–214 (1995).
Dabholkar et al., J. of Clin. Invest., Inc., 94:703–708, (1994).
Aziz Sancar, Science, 266:1954–1956 (1994).
van Duin et al., Nucleic Acids Research, 15:9195–9213 (1987).
van Duin et al., Cell, 44:913–923 (1986).
Dabholkar et al., Cancer Research, 55:1–6 (1995).
Jan H.J. Hoeijmakers, J. Cell Sci. Suppl. 6:111–125 (1987).
Salles et al., Toxicology 93:235–247 (1994).
Taverna et al., Carcinogensis 15:2053–2056 (1994).
Hill et al., Fur. J. Cancer 30A:832–837 (1994).
Lee et al., Carcinogenesis 14:2177–2180 (1993).
C.J. Jones and R.D. Wood, Biochemistry 32:12906–12104 (1993).
McDowell et al., Mutagenesis 8:155–161 (1993).
Dabholkar et al., Mutation Res. 293:151–160 (1993).
Gelenziunas et al., J. Natl. Cancer Inst. 83:557–564 (1991).
Tanaka et al., Nature 348:13–14 (1990).
Chu et al., Prog. Clin. Biol. Res. 304A:275–282 (1990).
Fraval et al., Mutation Res. 51:121–132 (1978).
C.H. Park and A. Sancar, Proc. Natl. Acad. Sci. USA 91:5017–5021 (1994).
C.H. Park and A. Sancar, Nucl. Acids Res. 21:5110–5116 (1993).
J. Bramson and L.C. Panasci, Cancer Res. 53:3237–3240 (1993).
Martin–Gallardo et al., Nat. Genet. 1:34–39 (1992).
Dabholkar et al., J. Natl. Cancer Inst. 84:1512–1517 (1992).
N. Sheibani and A. Eastman, Cancer Lett. 52:179–185 (1990).

*Primary Examiner*—Carla J. Myers
*Attorney, Agent, or Firm*—Birch, Stewart, Kolasch & Birch, LLP

[57] ABSTRACT

Assay of the mRNA levels of ERCC1 and XPAC, two genes whose products are involved in DNA repair, provides a method for determining the sensitivity of tumors to treatment by platinum-based chemotherapy. Tumors that are resistant to cisplatin tend to express high levels of the mRNA for ERCC1 which includes exon VIII. In some tumor types, concurrent expression of ERCC1 and XPAC mRNAs is also an indicator of cisplatin resistance.

13 Claims, 11 Drawing Sheets

BLOT #1  RESPONDERS
PATIENT # 1 2 3 4 5 6 7 8 9 10 11

ERCC1

XPAC

β-ACTIN

BLOT #2  NON-RESPONDERS
PATIENT # 12 13 14 15 16 17 18

ERCC1

XPAC

β-ACTIN

BLOT #3  (RESPONDERS) AND NON-RESPONDERS
PATIENT # (19) 20 21 22 (23)(24)(25) 26 27 28

ERCC1

XPAC

β-ACTIN

Total ERCC1

Full-Length ERCC1        268 bp
ERCC1 w/o Exon VIII                          196 bp

ß-ACTIN

Cell Lines    1  2  3
              |  |  |
           HuT 78 H9 MOLT-4

XPA

ß-ACTIN

Cell Lines    1  2  3
              |  |  |
           HuT 78 H9 MOLT-4

ASSAY FOR SENSITIVITY OF TUMORS TO DNA-PLATINATING CHEMOTHERAPY

BACKGROUND OF THE INVENTION

1. Field of the Invention

The invention relates to assessment of a genetic trait of tumor cells of a patient. The resistance of the tumor cells to chemotherapeutic agents which act by damaging DNA, especially agents which damage DNA in the manner of platinating agents (e.g., cisplatin, carboplatin), is assayed by examining the mRNA expressed from genes involved in DNA repair in humans.

2. Related Art

Excision repair of bulky DNA adducts, such as those formed by cisplatin, appears to be mediated by an aggregate of genes, with ERCC and XP proteins being involved in DNA damage recognition and excision (1–3). The human DNA repair genes ERCC1 (the human excision repair gene cross-complementing Chinese hamster ovary (CHO) mutant cell lines of complementation group I) and XPAC (the human excision repair gene that corrects the defect in xeroderma pigmentosum group A cells) have been cloned (4,5). Several studies using mutant human and hamster cell lines that are defective in either of these genes, and their transfected derivatives, and studies in human tumor tissues indicate that the products encoded by these genes are involved in the excision repair of platinum-DNA adducts (6–9).

The ERCC1 gene exhibits homology to the yeast RAD10 gene (19), which forms an endonucleolytic complex with RAD1, and is involved in the excision of bulky DNA adducts (11, 12). When transfected into DNA-repair deficient CHO cells, ERCC1 confers cellular resistance to cisplatin along with the ability to repair platinum-DNA adducts (9).

The relative levels of expression of excision repair genes in malignant cells from cancer patients receiving platinum-based therapy has been examined (6). Currently accepted models of excision repair suggest that the damage recognition/excision step is rate-limiting to the excision repair process. Studies of the homology of human excision repair genes with bacterial and yeast excision repair genes suggest that ERCC1 and XPAC may be the genes primarily involved in the recognition and excision of bulky DNA adducts (5, 10–12). This occurs with the help of putative helicases encoded by ERCC2, ERCC3, and ERCC6 (2,13).

A general review of the mechanism of excision repair has recently been published (36). In particular, it is known that the XPAC gene product associates with the ERCC1 gene product to form part of a protein complex that initiates excision repair (36, 37). As noted above, the ERCC1 gene has been cloned and its exon/intron structure is known (39). The structure of the ERCC1 gene is shown in FIG. 1 and the nucleotide sequence of the full-length cDNA can be found in reference 19. The ERCC1 mRNA is known to be produced in several forms in vivo. Geleziunas et al. have shown that transcripts of 1.1, 2.6, 3.4 and 3.8 kilobases (kb) length are found in chronic lymphocytic leukemia cells. Geleziunas et al. have also shown that the amount of the 1.1 kb transcript is correlated with resistance to nitrogen mustards, which alkylate DNA (30). Furthermore, an alternative splicing of the mRNA to include or eliminate exon VIII has been shown (38).

SUMMARY OF THE INVENTION

The present method assesses levels of expression of ERCC1 mRNA, especially a form of ERCC1 mRNA including exon VIII, and XPAC mRNA in tumor cells. The levels of an alternatively spliced species of ERCC1 mRNA which does not contain exon VIII are also measured. The present invention resides in part in the finding that the amount of ERCC1 mRNA which includes exon VIII is correlated with resistance to DNA platinating agents. Tumors expressing high levels of the form of the ERCC1 mRNA that includes exon VIII (exon VIII⁺ form) are considered likely to be resistant to platinum-based chemotherapy. By the same token, those tumors expressing significant amounts of the form of ERCC1 mRNA that lack the exon VIII (exon VIII⁻) form, are likely to be sensitive to platinum-based chemotherapy.

It has also been found that the relative total levels of XPAC mRNA and ERCC1 mRNA correlate with resistance to DNA platinating agents. Tumors having nearly equal levels of ERCC1 and XPAC mRNA are considered likely to be resistant to platinum-based chemotherapy. On the other hand, tumors having lower levels of ERCC1 mRNA than XPAC mRNA, especially tumors having differences about 5-fold or greater (i.e. a ratio of ERCC1 to XPAC mRNAs of about 0.2 or lower), are considered likely to be sensitive to platinum-based chemotherapy.

Accordingly, it is the object of the invention to provide a method for assessing the probable resistance of a tumor of a patient to treatment with DNA damaging agents, which agents create the type of lesions in DNA that are created by DNA platinating agents, by examination of the amount and forms of the mRNA for ERCC1 in the tumor cells.

BRIEF DESCRIPTION OF THE DRAWINGS

FIG. 3A shows the correlation between relative expression levels of total XPAC and ERCC1 mRNA in ovarian tumor tissues from patients responding to platinum-based therapy. FIG. 3B shows the correlation from patients not responding. Correlations were obtained by simple curve-fit analysis of the data.

DETAILED DESCRIPTION OF THE INVENTION

Figure 1:
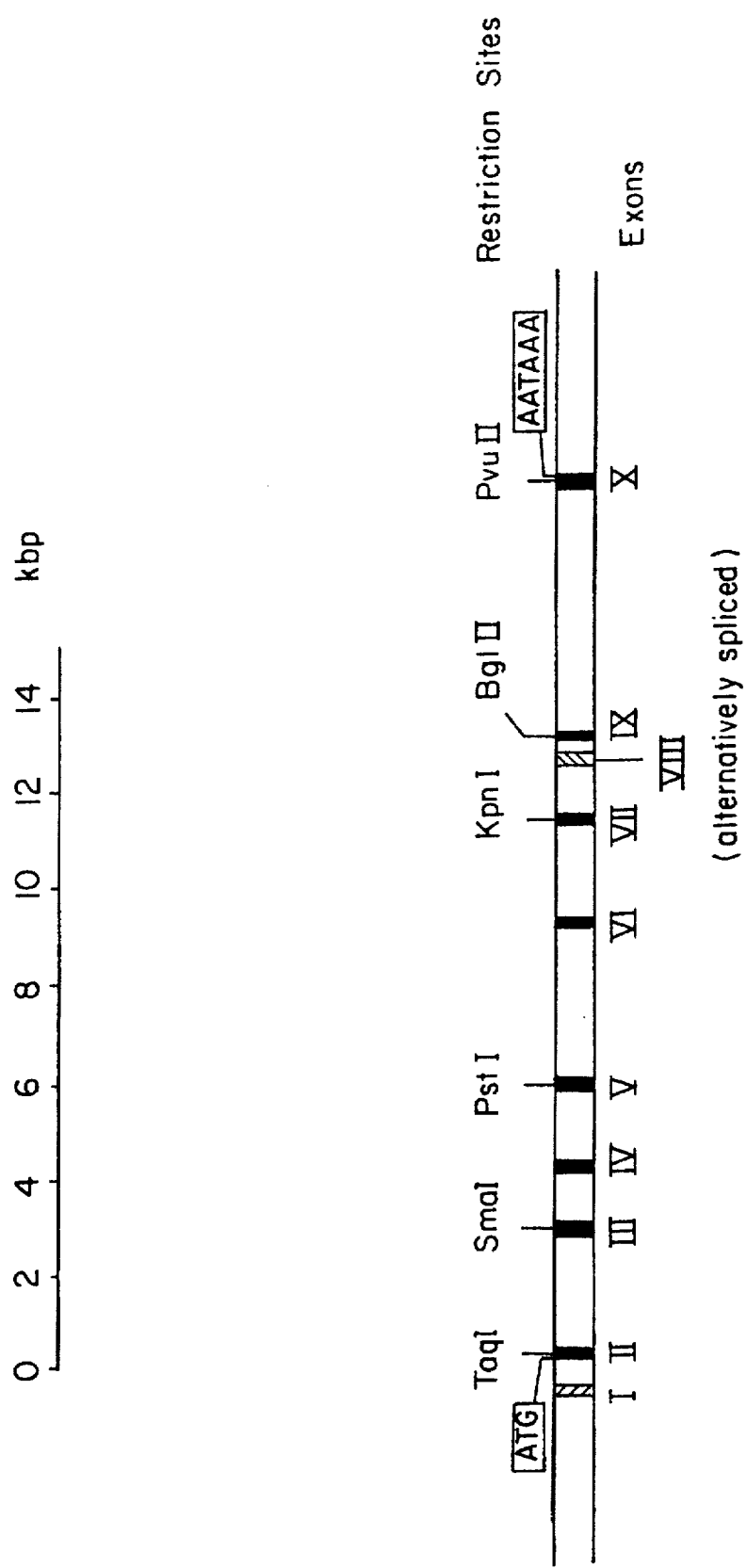
FIG. 1 [adapted from ref. 39] shows the gene structure of the ERCC1 gene. Protein coding exons II to VII and IX and X are shown as black boxes. Alternatively spliced exon VIII is shown as a hatched box. Restriction sites are shown above the map. The initiator ATG and terminator AATAAA are indicated. Note that exon I, (also a hatched box) represents 5' untranslated mRNA.

The present inventors have examined the details of expression of ERCC1 in tumor tissues, finding that expression of a particular form of the ERCC1 mRNA is significantly correlated with clinical resistance to platinum-based chemotherapy. In particular, expression of high levels of ERCC1 mRNA including exon VIII are correlated with resistance. The present inventors have also found that patients having tumors exhibiting a low level of XPAC mRNA, compared to total ERCC1 mRNA, tend to be more responsive to platinum-based chemotherapy.

For the purposes of this paper, "full-length" ERCC1 mRNA is ERCC1 mRNA which includes exon VIII. "Alternatively spliced" ERCC1 mRNA is ERCC1 mRNA which lacks exon VIII.

The tissues to which the present method can be applied are of any type. For examination of resistance of tumor tissue, of course the tumor tissue should be examined. It might be desired to also examine a portion of normal tissue from the patient from which the tumor is obtained, as patients whose normal tissues are expected to be resistant to platinum-based chemotherapeutic compounds, but whose tumors are expected to be sensitive to such compounds, could then be treated with higher amounts of the chemotherapeutic composition.

The method of the present invention can be applied to tumors of any type, but is preferably applied to solid tumors, most preferably ovarian tumors. For application of some embodiments of the invention to particular tumor types, it is preferable to confirm the relationship of the measurement to clinical resistance by building a preliminary database of the correlation of the particular ERCC1 expression parameter measured and clinical resistance to platinum-based chemotherapy. For example, the measurement of the relative levels of ERCC1 and XPAC mRNA does not correlate well in T cells, but correlates well in ovarian tumors. However, the correlation of the presence of exon VIII⁻ ERCC1 mRNA with sensitivity of cells to cisplatin correlates well in both T cells and in ovarian tumors.

To perform the method of the present invention, cells of the tumor are preferably isolated from the patient. Solid or lymphoid tumors are surgically resected from the patient. If blood tumors are examined, the practitioner should attempt to isolate the tumor cells being malignant blood cells from such normal blood cells as are present in the sample, for example by leukophoresis or centrifugation in a separation medium such as FICOLL HYPAQUE™.

The RNA is extracted from the cells by any of the methods typical in the art. If a hybridization method is used, it is preferable to isolate mRNA from the total RNA, again using methods common in the art. Preferably, care is taken to avoid degradation of the RNA during the extraction process.

The amount of ERCC1 mRNA can be measured by either Northern blotting or by polymerase chain reaction (PCR) methods. If Northern blotting is used, a probe from a portion of the ERCC1 mRNA that is not alternatively spliced will reveal the relative amounts of each of the alternatively spliced forms of the mRNA. In practice of the present method, the electrophoretic gel used to separate the mRNA samples by length should be one wherein species differing in size by 50 bp are well resolved. This is accomplished most easily by adjusting the gel concentration and composition so to optimize separation in the 500 bp to 5000 bp range (23). Alternatively, blots can be hybridized with probes containing sequences of particular exons in order to examine the amount of mRNA containing a particular exon.

For PCR analysis of the mRNA, the various forms of the ERCC1 mRNA can be examined by use of a single primer pair wherein the upstream and downstream primers are both located in regions of the ERCC1 mRNA that are 5' and 3' of the alternatively spliced portion of the ERCC1 mRNA, respectively (see FIG. 1). Such flanking primers are chosen to preferably bind to the mRNA within 250 bases of the exon VIII (or other exon which is being examined as to alternative splicing), and more preferably are chosen to bind within 150 bases, most preferably in the range 15 to 75 bases of the exon VIII. Alternatively, the amount of mRNA including a particular exon can be examined by choosing one of the primers so that it hybridizes to a site within the exon of interest. XPAC mRNA is examined in a similar manner.

The primers can be of any length which is sufficient to provide specific binding to the mRNA to be analyzed. The length of the primers is preferably less than 50 bases, more preferably less than 30 bases and most preferably in the range of 10 to 20 bases.

Of particular interest in the practice of the present invention is examination of exon VIII of the ERCC1 mRNA. Thus, primers are preferably chosen so that at least the amount of exon VIII⁺ ERCC1 mRNA can be measured. In some embodiments of the invention only the amount of ERCC1 that includes the exon VIII mRNA is measured. In other embodiments, the amount of mRNA including exon VIII is compared to the amount of XPAC mRNA present in the tumor. In still other embodiments of the invention, the amount of exon VIII⁻ ERCC1 mRNA is measured. Since the size of exon VIII of the ERCC1 mRNA is but 72 bp, methods relying upon separation of the VIII⁺ from the VIII⁻ forms of PCR products must be able to resolve the PCR products at this level of resolution.

It is considered that methods for quantitative measurement of mRNA by PCR and Northern blotting are known in the art. Any of such methods, including any methods which might rely upon primer-ligations, wherein short primers that abut a splice site are ligated after hybridizing to the mRNA, so that the ligated primer remains bound to the mRNA during the PCR cycle, but the unligated primer melts off, can also be used to practice the present invention. When performing the method of the invention using PCR analysis, the practitioner is also cautioned to take the necessary steps to prevent contamination of RNA samples by genomic DNA from the tissue and also to avoid cross-contamination between samples. Such precautionary methods are also considered well-known in the art.

From the measurement of the amount of XPAC mRNA compared to the amount of ERCC1 mRNA or from the amount of exon VIII⁺ ERCC1 mRNA that is expressed in the tumor, one can make a prognosis concerning clinical resistance of a tumor to platinum-based chemotherapy or to a chemotherapy inducing a similar type of DNA damage. Platinum is considered to cause a "bulky adduct" of the DNA, wherein the primary effect is to distort the three-dimensional conformation of the double helix.

The invention being thus described, practice of the invention is illustrated by the experimental examples provided below. The skilled practitioner will realize that the materials and methods used in the illustrative examples can be modified in various ways. Such modifications are considered to fall within the scope of the present invention.

EXAMPLE 1

Methods

Tissues studied. Fresh tumor tissues were obtained from 28 patients with ovarian cancer. These tissues were obtained before treatment with cisplatin- or carobplatin-based chemotherapy. Patients from whom tissues were obtained participated in either of three approved experimental treatment protocols for advanced stage ovarian cancer that have been reported previously by the Medicine Branch of the National Cancer Institute (14–16). Disease was followed by physical exam and by radiographic means, including abdominopelvic CT scan and/or ultrasound examination.

Complete response was defined as complete eradication of all evaluable disease, confirmed by peritoneoscopy. Partial response was defined at a >50% reduction in the sum of the products of the perpendicular diameters in all measurable lesions lasting at least 1 month. Progressive disease was a >25% increase in the sum of the products of the perpendicular diameters of all measurable lesions or the appearance of new lesions. Stable disease included those clinical circumstances which did not fit the definitions of objective response nor progression. Progressive disease and stable disease patients are included in the nonresponder category. Complete response and partial response are included in the responder category. By these criteria, there are 15 patients who were responders and 13 nonresponders in the cohort.

In vitro studies were performed using the ovarian cancer cell line A2780/CP70, which has been described previously by our laboratory (17).

PCR analyses. A reverse transcription/polymerase chain reaction (RT/PCR)-based assay system (6) was used to determine the level of expression of ERCC1, XPAC, and β-actin. Tissues were stored at −80° C. and extracted for total RNA by hot phenol/chloroform extraction (18). cDNA was obtained from 10 µg of total RNA by reverse transcription using oligo-dT primers (Reverse Transcription System; Porthega Corp., Madison, Wis.). cDNAs were washed and concentrated by ultrafiltration (Amicon, Beverly, Mass.) and resuspended to 100 µl in low TE buffer (10 mM Tris, pH 8.0, and 0.1 mM EDTA).

For ERCC1, primers and RT/PCR conditions were selected to affect amplification of a 481 hp segment from 245 to 725 of the ERCC1 cDNA nucleotide sequence (19) and including exon III to VI of the ERCC1 gene (ref. 20 and FIG. 1). The upstream (sense) primer had the nucleotide sequence 5'-GAGCTGGCTAAGATGTGTATCC-3' (SEQ. I.D. NO. 1). The downstream (antisense) primer for examination of the differential splicing of exon VIII⁺ had the nucleotide sequence 5'-AGGCCAGATCTTCTCTTGATGC-3' (SEQ. I.D. NO. 2). The downstream (antisense) primer for measurement of total ERCC1 mRNA had the sequence 5'-TCATAGGCCTTGTAGGTCTCCAGGTA-3' (SEQ. I.D. NO. 3).

For XPAC, primer and PCR conditions were optimized for amplification of a 531-bp segment from base 164 to base 694 (5) which spans a region that extends from within exon I to exon V (21). Primers chosen for β-actin spanned a 731-hp segment of the coding region of the β-actin gene and extended from base 269 of exon II to base 1535 in exon IV (22).

Aliquots of 7.5 µl of the cDNA preparation from each sample were thus amplified by RT/PCR for 30 cycles for ERCC1 and for β-actin and for 50 cycles for XPAC. The GeneAmp FCR reagens kit with AmpliTaq DNA polymerase (Perkin-Elmer Cetus Instruments, Norwalk, Conn.) was used for each gene. Aliquots of amplified DNA were electrophoresed through a 1.5% agarose gel. Amplified DNA was visualized by ethidium bromide staining, photographed over an ultraviolet (I/V) transilluminator (Hoefer Scientific Instruments, San Francisco, Calif.), and transferred to Hybond N+ membrane (Amersham International, Buckinghamshire, UK) Oligonucleotides (26-mers) from the central region of each amplified sequence were end-labeled with [$^{32}$P]τ-ATP (Amersham International) using T4 polynucleotide kinase (Stratagene, La Jolla, Calif.) and were used as the respective probes. Oligonucleotides used as primers and probes for RT/PCT-based analysis of ERCC1 expression were synthesized on a DNA synthesizer (Biosearch, Inc., San Rafael, Calif.) and purified by polyacrylamide gel electrophoresis (23). Primers and probes for XPAC and β-actin PCRs were synthesized by Lofstrand Laboratories, Ltd. (Gaithersburg, Md.).

Numerical values for the expression of the ERCC1 and XPAC genes in tumor tissue specimens were obtained as follows. For each sample, the densitometric readout of the autoradiographic signal generated by the RT/PCRs-amplified DNA when hybridized to 32P-labeled ERCC1 or XPAC probe was divided by the densitometric reading for β-actin. For purposes of comparison, the sample with the highest ERCC1/actin value was assigned the value of 1, and all other samples were expressed relative to that value. For XPAC expression, the sample with the highest XPAC/actin value was assigned the value of 1, and the other samples were expressed relative to this value.

Aliquots of 3 µl of the cDNA preparation from samples expressing detectable levels of ERCC1 RT/PCR product were analyzed for alternative splicing of ERCC1. Primers flanking exon VIII, which is 72 bases long, were used to detect the presence and relative proportions of full length and alternatively spliced ERCC1 cDNA sequence extending from base 692 to base 959 (19). RT/PCR was conducted for 30 cycles. Southern blots of amplified segments were hybridized with a probe 26 bases long extending from base 764 to 789, 5' of exon VIII. The ratio of autoradiographic signals thus generated to the autoradiographic signal obtained for β-actin for each sample was used to determine the levels of the full length ERCC1 mRNA (with the 72-base-long exon VIII) and an alternatively spliced species of ERCC1 mRNA (without exon VIII). When assessing alternative splicing of ERCC1 mRNA, the human T lymphocyte cell line, H9 (24), was used as an internal control.

Statistical analyses. The relationship between response to therapy and expression of excision repair genes was examined for statistical significance using the Student's t test with the Statworks program on a Macintosh SE Computer (Apple Computers, Inc., Palo Alto, Calif.). Two-sided P values are shown in the tables and text. Curve fitting analyses to obtain correlation coefficients were similarly conducted using the CricketGraph program (Computer Associates International, Inc., Islandia, N.Y.).

Results

Figure 2:
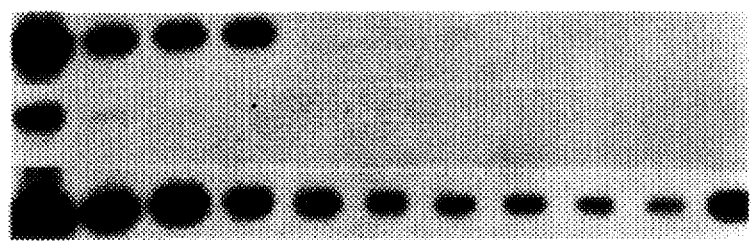
FIG. 2 shows autoradiographs generated by RT/PCR-amplified RNA from ovarian cancer tissues after hybridization of Southern blots with radiolabeled probes for ERCC1, XPAC and β-actin. Samples 1–11, 19 and 23–25 (blots 1 and 3) represent tumor tissues from patients responding to platinum-based therapy; samples 12–18, 20–22 and 26–28 (blots 2 and 3) represent 13 tumor tissues from patients resistant to platinum-based therapy.
Figure 2:
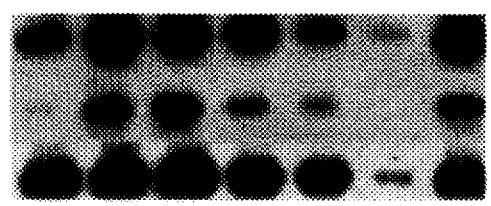
Figure 2:
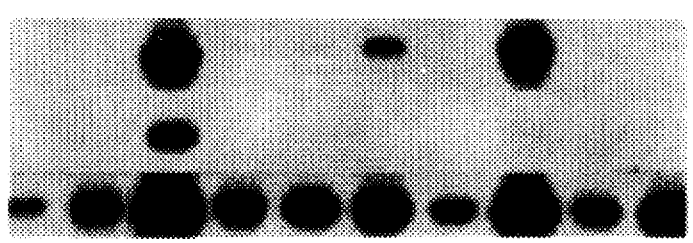

FIG. 2 shows autoradiographs of RT/PCR-amplified mRNA from the 28 patients studied in the cohort. Detectable levels of ERCC1 mRNA were seen in 19 tumor specimens. Detectable levels of ERCC1 were seen in 11 out of 13 tumors that were resistant to therapy, but in only 7 out of 15 tumors that were clinically sensitive to therapy. For XPAC, detectable mRNA levels were seen in 8 out of 15 nonresponders and in 2 out of 13 responders.

The median level of ERCC1 expression for the cohort of 28 patients was 0.18; and for XPAC the median level of expression was not detectable (<0.01). When responders and nonresponders are assessed as a function of the median expression levels of these two genes, higher levels of expression were consistently seen in the nonresponder group. In nonresponders, 9 out of 13 showed ERCC1 levels higher than the median, and 6 out of 13 showed XPAC levels higher than the median. In responding patients, 5 out of 15 showed ERCC1 levels higher than the median, and 2 out of 15 showed XPAC levels higher than the median. Concurrent expression levels for both genes, which were higher than the median, were seen in 8 out of 13 tumors that were clinically resistant to platinum-based therapy and in 2 out of 15 tumors that were clinically sensitive.

Table I shows the summary values for ERCC1 and XPAC for responders and nonresponders. The difference between disease response groups for XPAC is statistically significant (P=0.011), but for ERCC1 the relationship borders on significance (P=0.059).

TABLE I

RELATIVE LEVELS OF ERCC1 AND XPAC GENE EXPRESSION IN OVARIAN TUMOR TISSUE IN RELATION TO RESPONSE

| | Range | Median | Mean ± SD |
|---|---|---|---|
| ERCC1 | | | |
| Responders (n = 15) | <0.01–1.00 | <0.01 | 0.21 ± 0.32 |
| Non-Responders (n = 13) | <0.01–0.94 | 0.50 | 0.46 ± 0.34 |
| | | | P = 0.059 |
| XPAC | | | |
| Responders (n = 15) | <0.01–0.45 | <0.01 | 0.03 ± 0.12 |
| Non-Responders (n = 13) | <0.01–1.00 | 0.09 | 0.31 ± 0.37 |
| | | | P = 0.011 |

Figure 3A:
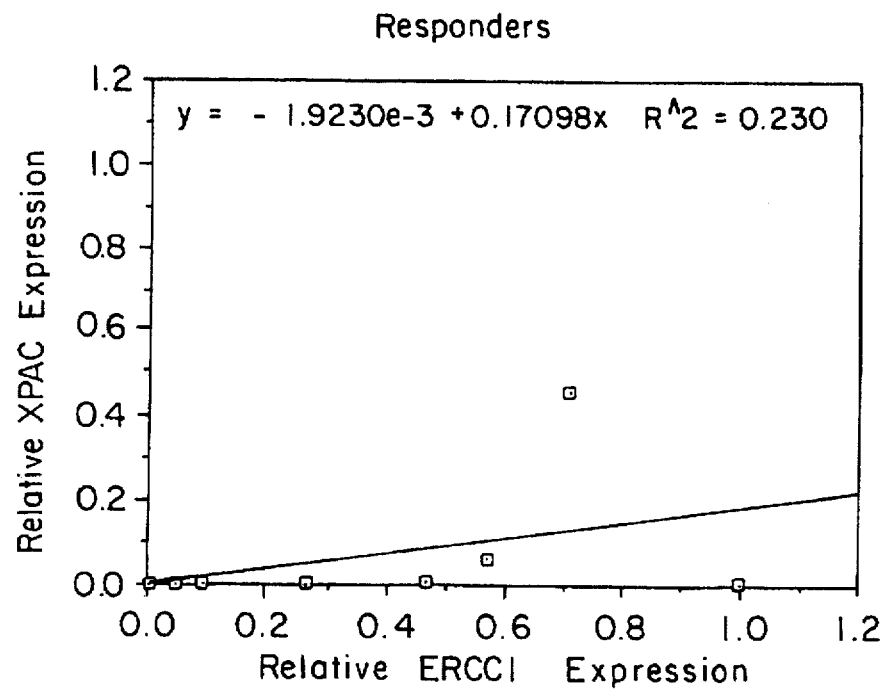
FIGS. 3A–B show expression of XPAC and ERCC1 mRNA in ovarian tumor tissues.
Figure 3B:
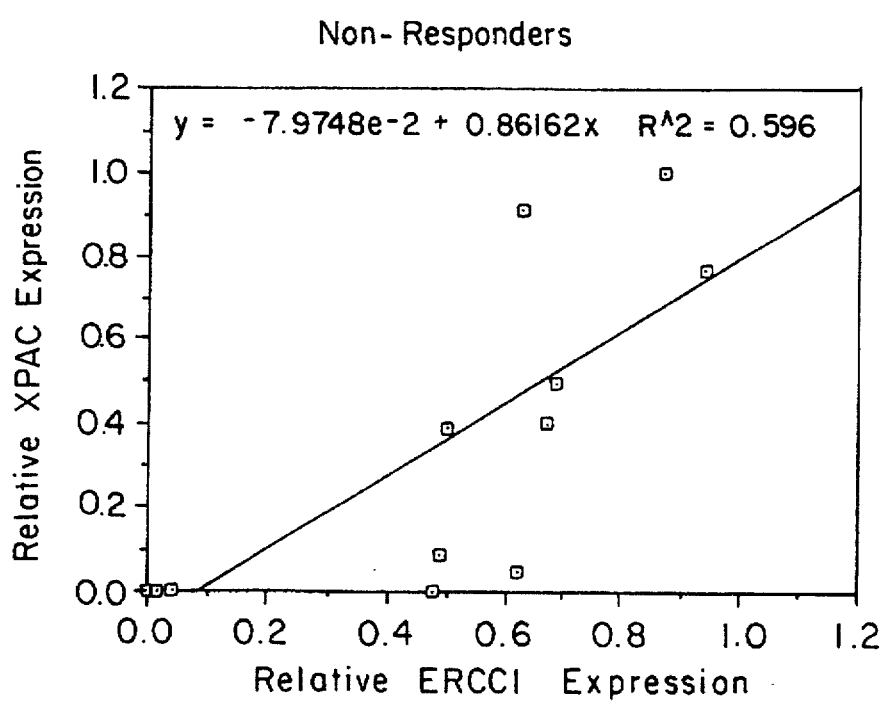

FIG. 3 shows the graphic relationship between ERCC1 and XPAC for responding patients (3A) and for nonresponders (3B). For tumors sensitive to platinum-based therapy, XPAC expression is consistently extremely low regardless of the ERCC1 level (FIG. 3A). For tumors resistant to platinum-based therapy, there is a suggestion of coordinated expression of these two genes in those tissues (FIG. 3B). In platinum-resistant tumors, the shift of the curve to the right suggests that ERCC1 expression may be upregulated first, followed by upregulation of XPAC.

Figure 4:
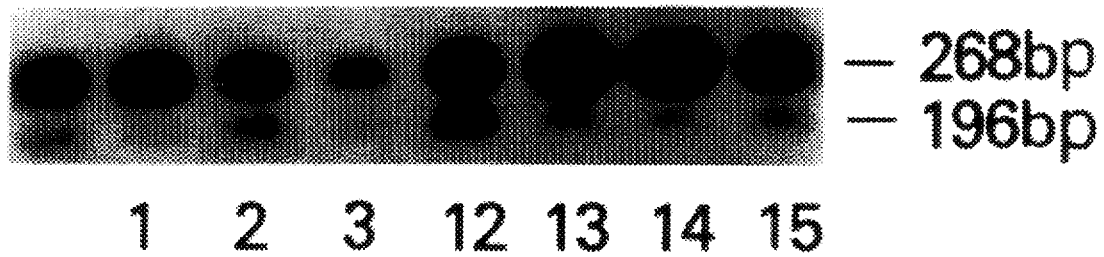
FIG. 4 shows alternative splicing of ERCC1 mRNA in 19 ovarian tumor tissues. Autoradiographs generated by Southern blots of amplified segments representing the full length transcript and the alternatively spliced (at exon VIII) species of ERCC1 mRNA are shown. Blots were hybridized with a probe extending from base 764 to base 789, 5' of exon VIII in the ERCC1 cDNA sequence. The numbers in the figure correspond to patient numbers as in FIG. 2.
Figure 4:
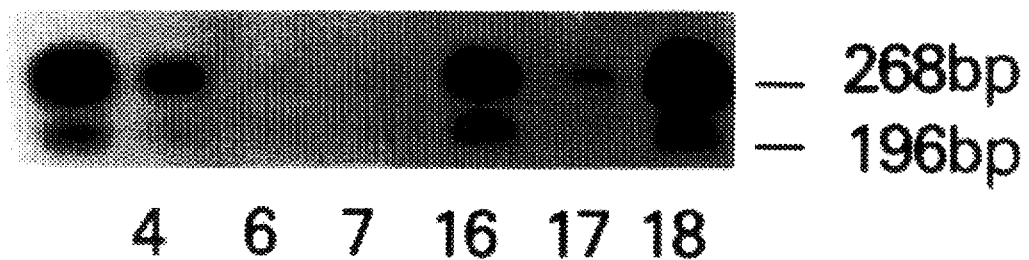
Figure 4:
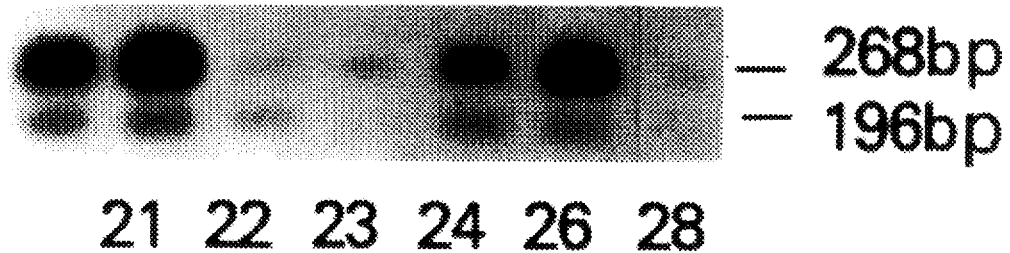

FIG. 4 shows autoradiographs of the 19 samples assessed for the full length transcript of ERCC1, as well as the alternatively spliced species. In both responders and nonresponders, expression levels of both species were highly variable. Table II shows a summary of the numerical values generated from FIG. 4. For the full length transcript of ERCC1, the difference between responders and nonresponders was statistically significant (P=0.026), whereas for the alternatively spliced species the difference only bordered on significance (P=0.058). Table II also shows a summary of the percentage of total ERCC1 which was lacking exon VIII in responding patients and in nonresponders. In responding patients, the percentage varied from 1.5 to 58.3%, and in nonresponders the percentage varied from 3.5 to 70.6%.

TABLE II

RELATIVE LEVELS OF ALTERNATIVELY SPLICED SPECIES OF ERCC1 mRNA IN OVARIAN TUMOR TISSUE IN RELATION TO RESPONSE

| | Range | Median | Mean ± SD |
|---|---|---|---|
| Full Length Transcript of ERCC1 | | | |
| Responders (n = 8) | 0.05–0.36 | 0.18 | 0.19 ± 0.12 |
| Non-Responders (n = 11) | 0.07–1.00 | 0.38 | 0.44 ± 0.27 |
| | | | P = 0.026 |
| Alternatively Spliced Species of ERCC1 | | | |
| Responders (n = 8) | 0.003–0.10 | 0.04 | 0.05 ± 0.04 |
| Non-Responders (n = 11) | 0.01–0.21 | 0.10 | 0.10 ± 0.07 |
| | | | P = 0.058 |
| Percentage of Total ERCC1 that is Alternatively Spliced | | | |
| Responders (n = 8) | 1.5–58.3 | 18.0 | 21.9 ± 17.9 |
| Non-Responders (n = 11) | 3.5–70.6 | 13.2 | 22.6 ± 20.0 |

A2780 CP70 cells were assessed for ERCC1 and XPAC mRNA expression, based on whether cells were in the exponential growth phase or in confluence. mRNA levels of XPAC were not different between exponentially growing cells and confluent cells. Surprisingly, mRNA levels of ERCC1 were slightly higher in confluent cells.

Discussion

DNA repair is one of the three major molecular mechanisms through which cells become resistant to platinum compounds (25). Studies in human ovarian cancer cells (17), in human T lymphocytes (26), and in murine T.1210 leukemia cells (27,28) all suggest that, at low levels of platinum resistance (up to 10–15-fold over baseline), DNA repair is the most important mechanism of resistance.

The DNA repair gene XPAC has generally been studied with respect to UV repair deficiency states such as xeroderma pigmentosum (29). This is the first study relating XPAC gene expression to the clinical treatment of a human malignant disease. ERCC1 has been studied in human ovarian cancer cells (6) and in chronic lymphocytic leukemia (30); but it was not determined in either study whether there was a relationship between processing of the RNA of the ERCC1 gene and tumor cell resistance to chemotherapy. Current models suggest that ERCC1 and XPAC may work together to recognize and excise covalent DNA damage from intact DNA (3, 36). This report suggests that in human ovarian cancer these two genes are directly related to clinical resistance to DNA-damaging platinum compounds and supports the concept that these two genes work together in this process.

The XPAC gene product exhibits homology to the bacterial and yeast proteins uvrA and RAD14, respectively (5,10). The section of XPAC mRNA that is amplified by PCR in our study, ranging from exon I to possibly exon V (21), includes segments of the XPAC protein that are essential for DNA repair function (31). These segments include a glutamic acid cluster in exon II that may bind histones and the DNA-binding zinc finger motif in exon III (31). The XPAC gene product is thus involved in the recognition of bulky DNA adducts and is essential for excision repair of bulky adducts (3,8,10). The impaired ability of XPA-derived fibroblast cell lines to effect the repair of platinum DNA adducts has been well documented (7,32,33). In our study, significantly higher levels of XPAC mRNA were detected in the tumor tissues of patients resistant to platinum-based therapy, compared with tissues from patients responding to therapy. This is the first study suggesting the clinical importance of high levels of XPAC gene expression in determining the ability of malignant tissue to process platinum DNA adducts.

Our present study indicates that concurrent high levels of expression of both ERCC1 and XPAC may translate into augmented tumor cell resistance to platinum-based therapy in ovarian cancer tissue. Concurrent expression of ERCC1 and XPAC mRNA occurs in the tumor tissues from patients resistant to platinum-based therapy. Thus, the concurrent augmentation in the expression of the XPAC and ERCC1 genes (which recognize and cleave bulky adducts) may result in the increased removal of DNA damage affected by platinum therapy. It is interesting to note that, in ovarian tumor tissue, upregulation of ERCC1 appears to occur before an upregulation of XPAC gene expression (see FIG. 3B). A similar relationship between ERCC1 and other ERCC genes was observed in nonmalignant bone marrow from cancer patients and also in human ERCC1-transfected CHO cells (34). In that study, the regulation of ERCC1 expression appeared to dictate the regulation of ERCC2 and ERCC6.

The presence of an alternatively spliced species of ERCC1 mRNA lacking a 72-bp exon was first reported in a study of poly(A) RNA from HeLa and K562 cell lines and of human ERCC1 cDNA clones (19). In that study, transfection experiments indicated that only the cDNA from the full human ERCC1 transcript (which includes exon VIII) could complement the excision repair defect for UV and mitomycin C.

For total ERCC1, the difference between responders and nonresponders had a P value of 0.059, and for nonfunctional ERCC1 the P value was 0.058. One report has suggested that the smaller "nonfunctional" transcript for ERCC1 may indeed have a "helper" function for the repair of UV and mitomycin C-induced DNA damage in some settings (35). The data presented in Example 2, below, suggest that the exon VIII$^-$ form of the ERCC1 mRNA might function in an dominant negative fashion. That is, the exon VIII$^-$ mRNA might encode a protein which actually inhibits the function of exon VIII$^+$ ERCC1. Since the P value for the full "functional" transcript for ERCC1 is 0.026, we believe that our clinical observations are consistent with the laboratory model regarding the function of the full transcript and of the full transcript lacking exon VIII.

The rate limiting step in DNA excision repair is the damage recognition excision step, which is mediated by genes of the ERCC and XP groups (3). Here, we have shown that mRNA levels of two of the key genes in this process, ERCC1 and XPAC, are directly related to clinical resistance to platinum compounds in human ovarian cancer. This suggests that the concurrent expression of both enzymes may increase the removal of the DNA damage effected by platinum therapy.

EXAMPLE 2

Methods

The expression of total ERCC1 mRNA, exon VIII$^-$ mRNA and XPA mRNA was examined in three human T lymphocyte cell lines (HuT 78, H9 and MOLT-4), using essentially the methods described in Example 1. The cells were obtained from the American Type Culture Collection, Rockville, Md. Cells were cultured in RPMI-1640 medium supplemented with 10% heat-inactivated calf serum, 100 µg/ml penicillin, 100 µg/ml streptomycin and 2 mM glutamine.

All cell lines were assayed for sensitivity to cisplatin by measurement of the inhibition of growth following 3 day cisplatin exposures ranging from 0.5 to 100 µM. Cell lines were seeded at an initial cell density of $5 \times 10^4$ cells/ml. After continuous contact with drug for 3 days, cell counts obtained by Coulter counter were expressed as a percentage of counts obtained from aliquots of control cells, cultured in the absence of drug. Cells treated similarly but for the absence of drug served as controls. IC$_{50}$ values were assessed as those drug levels effecting a 50% reduction in cell number as compared to Untreated cells.

The preparation and platination of plasmid DNA, transfection of plasmid into cells, preparation of cell lysates, the assay for CAT activity, and the measurement of the ability of cells to remove platinum from cellular DNA were performed as previously described (26). Numerical values for repair of cellular DNA and of plasmid DNA are taken from that manuscript (26).

Results

Figure 5:
FIG. 5 shows autoradiographs generated by RT/PCR-amplified RNA from three non-drug-selected T lymphocyte cell lines, HuT 78, H9, and MOLT-4, respectively following hybridization of Southern blots with radiolabelled probes for total ERCC1, full-length and alternatively spliced ERCC1, XPA, and β-actin.
Figure 5:
Figure 5:
Figure 5:
Figure 5:
Figure 6A:
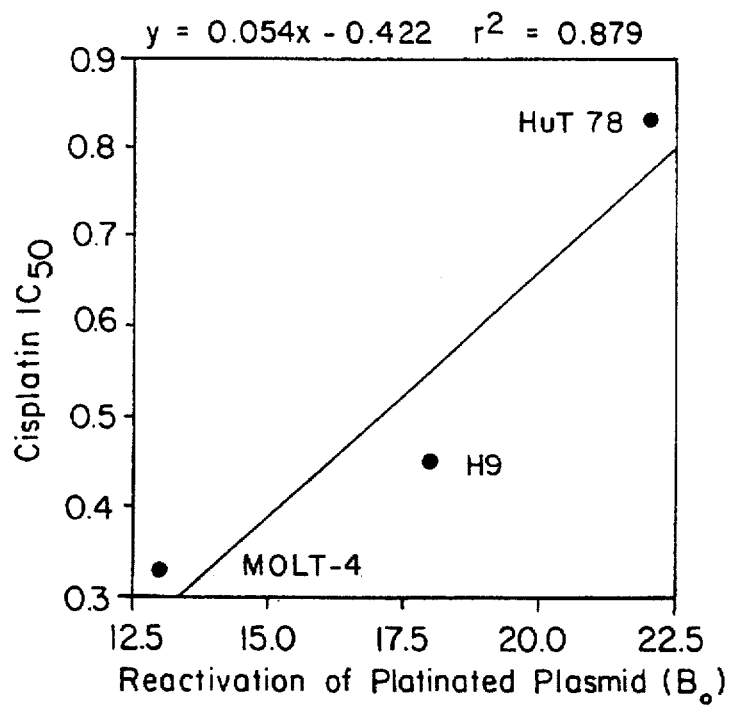
FIGS. 6A-B shows the relationship between cellular resistance to cisplatin in T cell lines and their ability to repair platinum-DNA adducts from plasmid DNA (FIG. 6A) and from cellular DNA (FIG. 6B).
Figure 6B:
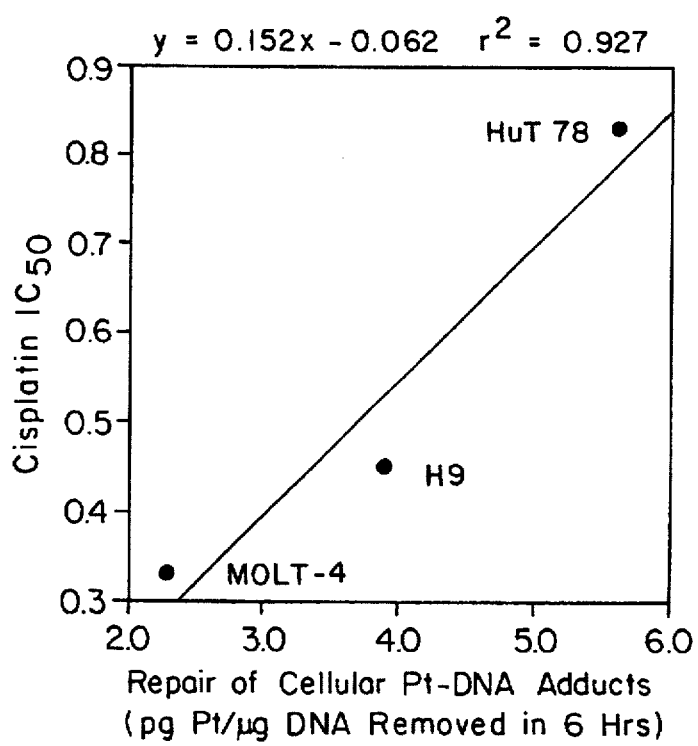

FIG. 5 shows autoradiographs of RT/PCR amplified mRNA for the excision repair genes ERCC1 and XPA, from the three T cell lines, with the β-Actin controls. Expression of total ERCC1 mRNA, XPA mRNA, and of the alternatively spliced ERCC1 transcript, are indicated in the Table III. Table III also includes data pertaining to the DNA repair capability of the three T cell lines, and their sensitivity to cisplatin (see also, ref. 26). The relative resistance of the three T cell lines to cisplatin is related to their DNA repair capability (Table III; FIG. 6). The ability of the cells to reactivate platinated plasmid is directly related to cellular resistance to cisplatin ($r^2=0.879$; FIG. 6A). The repair of platinum adducts from cellular DNA is directly related to cellular resistance to cisplatin ($r^2=0.927$; FIG. 6B).

TABLE III

DNA repair activity, cellular sensitivity to cisplatin, and expression of excision repair genes ERCC1, and XPA in three human T lymphocyte cell lines

| A<br>Cell<br>lines | B<br>Cisplatin<br>$IC_{50}$ (μM)<br>3 Days[a] | C<br>Reactivation<br>of platinated<br>plasmid<br>$B_o$[b] | D<br>Cellular DNA<br>Repair[c] (pg Pt/<br>μg DNA removed<br>in 6 hrs) | E<br>Total<br>ERCC1<br>mRNA | F<br>XPA<br>mRNA | H<br>ERCC1<br>mRNA<br>without<br>Exon VIII[d] |
|---|---|---|---|---|---|---|
| HuT 78 | 0.83 | 22 | 5.6 | 2.321 | 0.356 | 0.005 |
| H9 | 0.45 | 18 | 3.9 | 0.737 | 0.414 | 0.099 |
| MOLT-4 | 0.33 | 13 | 2.3 | 0.762 | 0.396 | 0.127 |

Figure 7A:
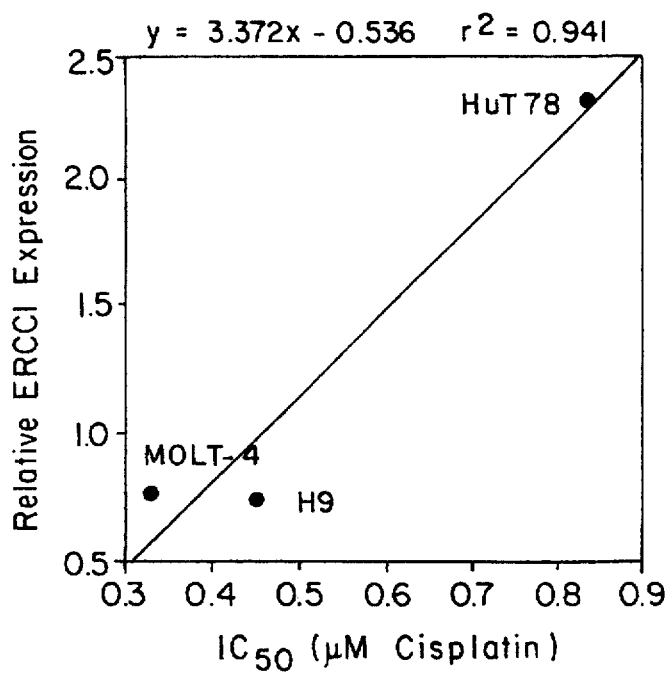
FIGS. 7A-C show the relationship between total ERCC1 mRNA levels and the repair of platinum-DNA adducts from cellular DNA (FIG. 7B), repair of plasmid DNA (FIG. 7C), and cellular resistance to cisplatin (FIG. 7A).
Figure 7B:
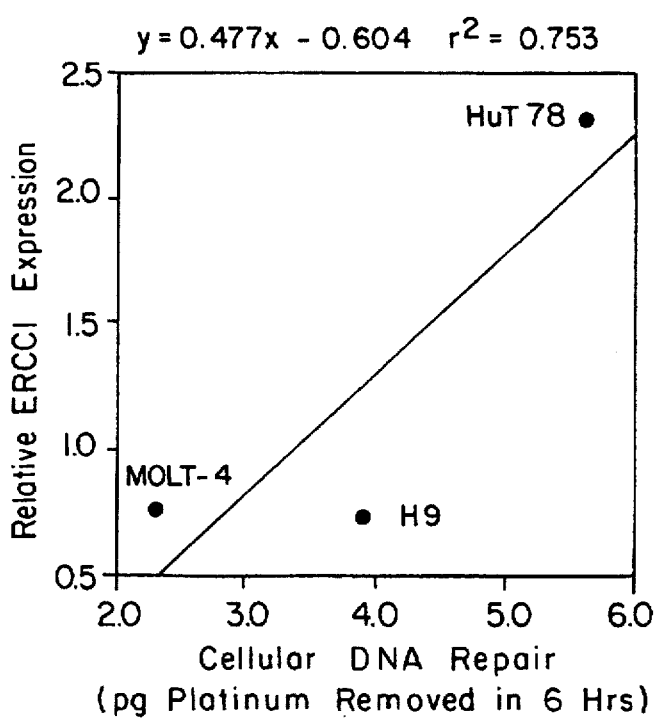
Figure 7C:
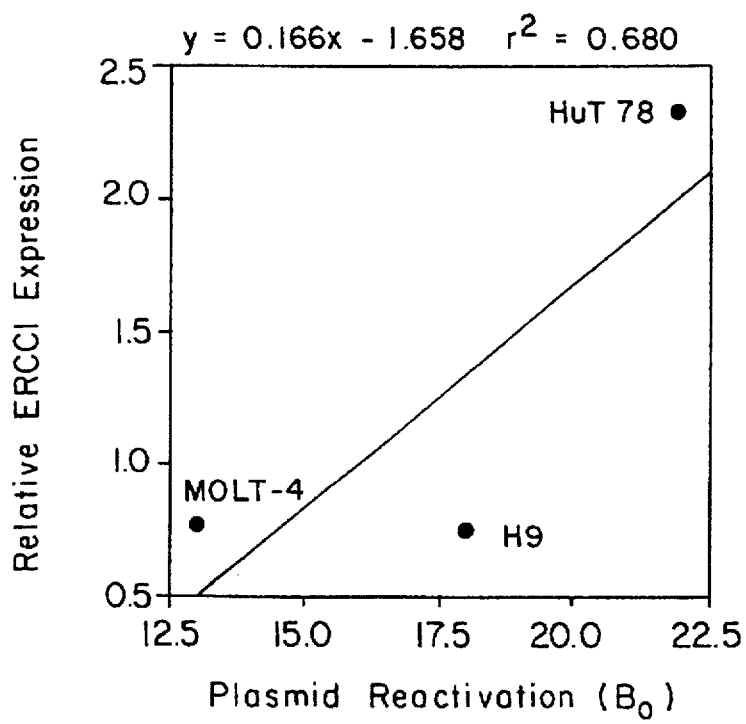

[a] Continuous exposure to cisplatin for 3 days
[b] Levels of plasmid platination (adducts/plasmid) that reduce CAT activity to 37% of control
[c] Platinum-DNA adducts removed from cellular DNA following a 1 hr, 10 μM exposure
[d] Alternatively spliced ERCC1 transcript FIG. 7 demonstrates the relationship between total ERCC1 mRNA levels in the three non-drug-selected T cell lines and repair of cellular DNA (7B), plasmid repair (7C), and resistance to cisplatin (7A). Total ERCC1 mRNA levels in the three T cell lines are directly related to their ability to effect repair of Pt-DNA adducts from cellular DNA ($r^2$=0.753); to their ability to reactivate platinated plasmid DNA ($r^2$=0.680); and to cellular resistance to cisplatin ($r^2$=0.941). This is consistent with our previous report suggesting that ERCC1 was essential in the repair of platinum-DNA adducts (9).

Figure 8A:
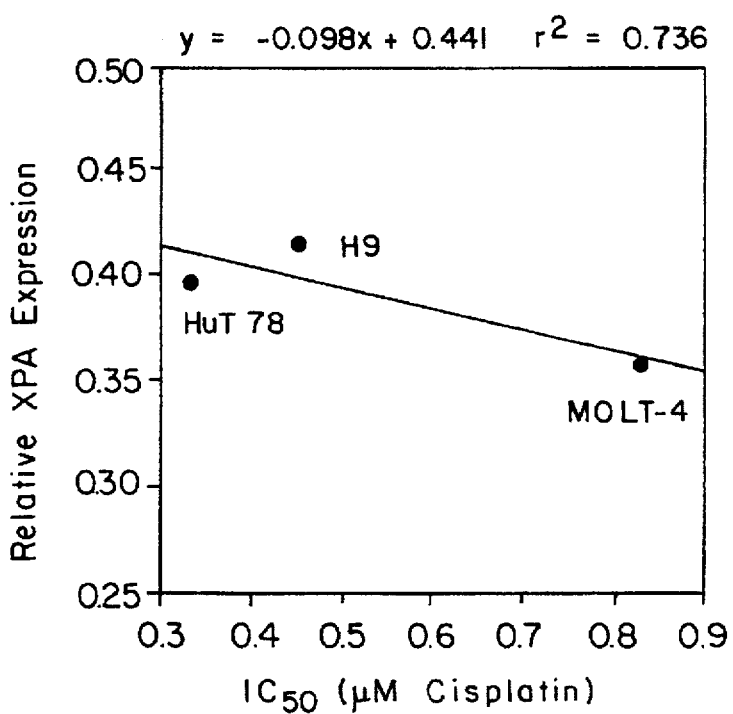
FIGS. 8A-C show the relationship between XPA mRNA levels and the repair of platinum-DNA adducts from cellular DNA (FIG. 8B), repair of plasmid DNA (FIG. 8C), and cellular resistance to cisplatin (FIG. 8A).
Figure 8B:
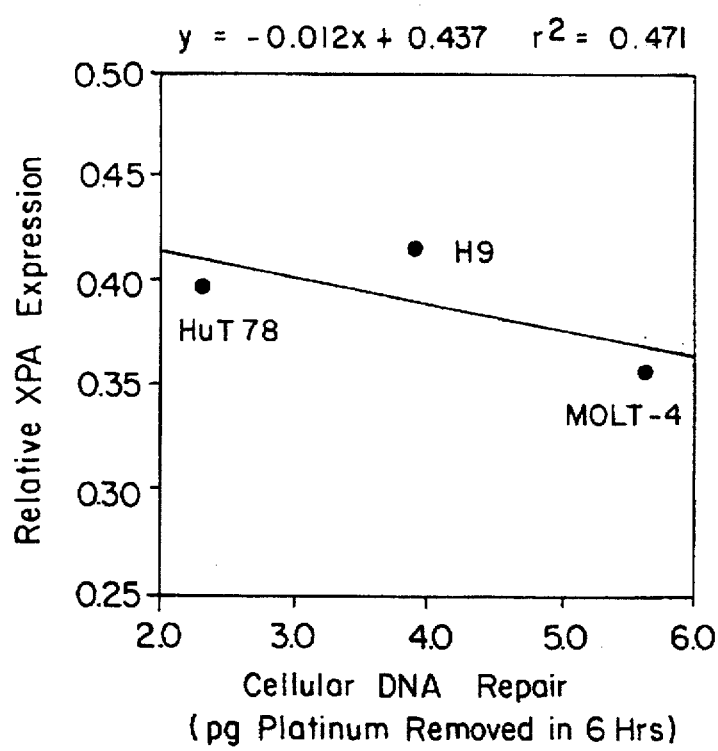
Figure 8C:
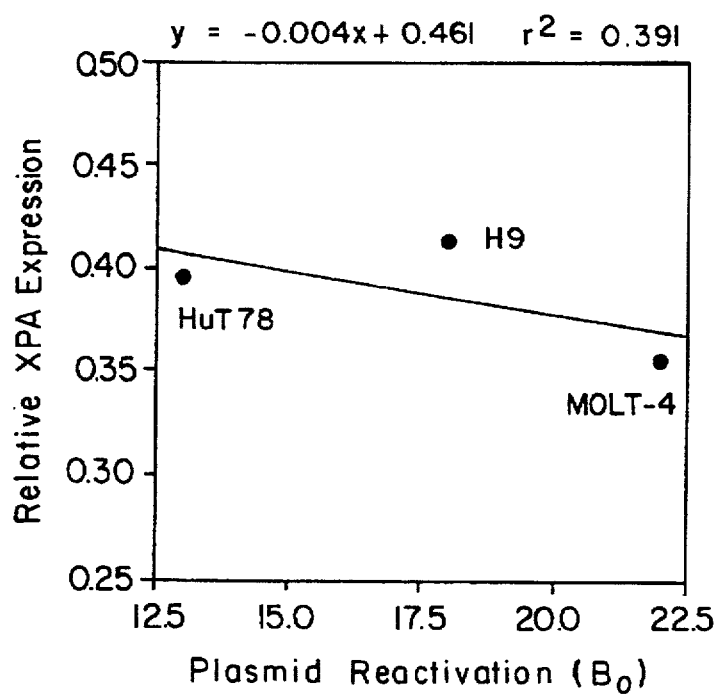

For XPA, approximately equal levels of mRNA were present in each cell line. There was therefore no relationship between XPA expression and cisplatin sensitivity/resistance (FIG. 8A), or repair of cellular DNA (FIG. 8B), or repair of plasmid DNA (FIG. 8C). As indicated in FIG. 8, cisplatin sensitivity varied by about 3-fold, as did repair of cellular DNA. Over this same range of variability in cisplatin sensitivity and in DNA repair, ERCC1 mRNA levels varied by about 3-fold (see FIG. 7).

Figure 9A:
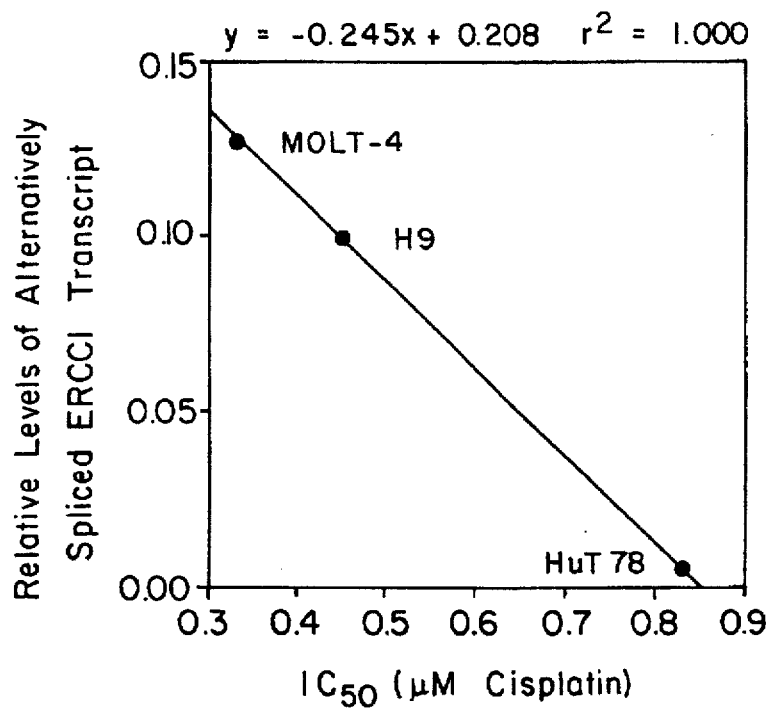
FIGS. 9A-C show the relationship between levels of the alternatively spliced ERCC1 transcript and the repair of platinum-DNA adducts from cellular DNA (FIG. 9B), repair of plasmid DNA (FIG. 9C), and cellular resistance to cisplatin (FIG. 9A).
Figure 9B:
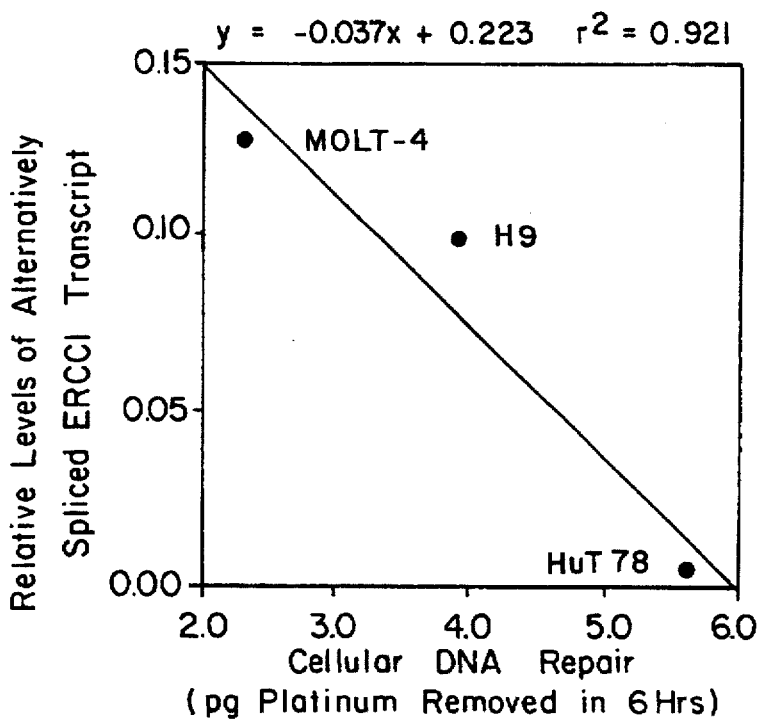
Figure 9C:
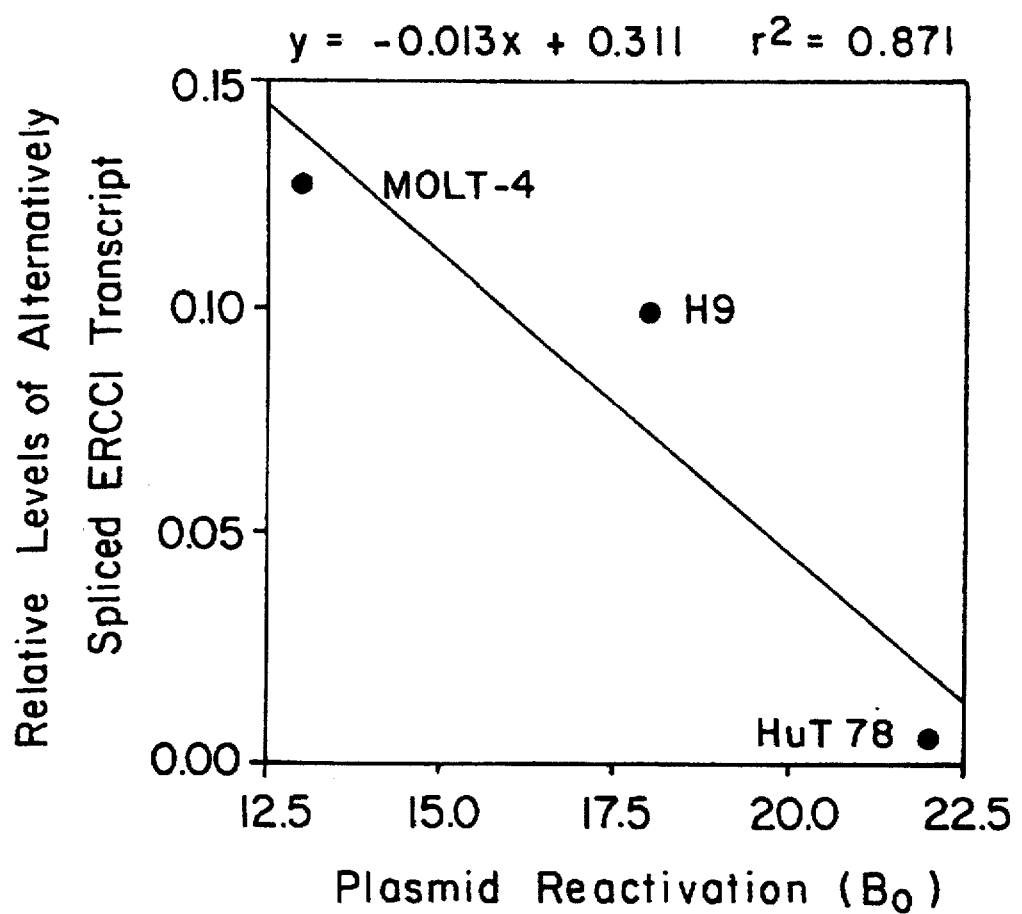

For the shortened transcript of ERCC1, expression levels varied by more than 20-fold. When the shortened transcript was barely detectable, DNA repair activity was at the greatest level. As mRNA levels of the shortened transcript increased, DNA repair activity decreased. This was the case whether repair was measured in cellular DNA (FIG. 9B) or in plasmid DNA (FIG. 9C). The relationship approached linearity in both cases, with correlation coefficients that exceeded the relationships between total ERCC1 and DNA repair, which are shown in FIG. 7.

Discussion

In non-drug selected human T lymphocytes, DNA repair activity is directly related to cellular resistance to cisplatin (26). In this system, neither cytosolic inactivation of drug nor transmembrane cellular accumulation of drug appear to be related to resistance (26). Such a system may be desirable for studying the role of various factors on the DNA repair process, as it relates to cisplatin resistance. The focus of these studies was to identify the possible relative roles of normal XPA, full-length ERCC1 and alternatively spliced ERCC1, in a system where DNA repair is the clear determinant of sensitivity/resistance to platinum compounds.

In this system, as has been reported in human ovarian cancer (38, 6), total ERCC1 expression is directly related to resistance to cisplatin. The analysis of the shortened "non-functional" transcript is even more interesting. When total "non-functional" ERCC1 mRNA is measured, the alternatively spliced species increases by more than 20-fold as cellular DNA repair is reduced from 5.6 picograms/μg DNA to 2.3 picograms/μg DNA (see Table III). Similarly, the repair of transfected plasmid DNA, measured by the $B_o$, is reduced by about half, concomitant with the 10-fold increase in the level of the shortened ERCC1 transcript. Both measurements in the changes in repair are related to a substantial reduction in cellular resistance (i.e., enhanced sensitivity) to cisplatin.

Alternative splicing is associated with inhibition of the function of the full length species for a number of other genes. For the c-myb protooncogene, an alternatively spliced mRNA species encodes a truncated protein that includes the DNA binding region and nuclear localization signal of the full length protein product but does not contain transcriptional regulatory regions; the truncated and full-length protein have opposing effects on cell differentiation (40). This type of negative interaction by a truncated protein has also been described for the Fos gene products as well as the E2 gene product of the bovine papillomavirus (41, 42).

The C-terminal part of ERCC1 appears to be crucial for its excision function (43). The stretch of 54 amino acids of ERCC1, which exhibit homology with the C-terminal region of uvrC, extend from amino acid 236 to 289 (44). The region of the protein encoded by exon VIII extends from amino acids 235 to 258 (45) and spans 23 of the 54 amino acids that are homologous to uvrC. The start of exon VIII appears to demarcate the initiation of the region of homology of ERCC1 with uvrC (43,45). The DNA-binding motif, however, constitutes a stretch of amino acids (133 to 153) that are about 80 amino acids 5' of exon VIII (45). Thus, the truncated ERCC1 protein, devoid of the 24 amino acids encoded by exon VIII, may retain DNA-binding ability and the ability to form a complex with other NER proteins, but may lack the ability to form incisions in DNA. The apparently negative influence of the alternatively spliced ERCC1 transcript on DNA repair capability, may be effected by the truncated protein competing with the full length protein for the DNA binding site, or by interfering with the formation of an effective protein complex that can excise the damaged DNA, after recognition and binding have occurred.

Compared to the results observed in Example 1, the correlation between ERCC1 mRNA levels and XPAC mRNA levels is weaker in the experiments shown in the present Example 2. The cells in this second system were three non-drug-selected T cell lines, rather than tumor tissue obtained from patients. Thus, measurement of the amount of ERCC1 mRNA, in particular the amount of exon VIII⁻ mRNA, appears to be the most broadly applicable indicator of sensitivity to platinum-based chemotherapy. The other measures of sensitivity to platinum-based chemotherapy seem to be better applied to specific tumor types for which a preliminary examination shows the correlations will hold.

The data of Example 2 also suggest, without binding the inventors to any theory of the invention, that ERCC1 might be the primary gene in the initial step of nucleotide excision repair (NER), and that XPA may be regulated in a secondary fashion. This might also suggest that biologically, XPA may have a "helper" function to ERCC1. Thus both XPA and ERCC1 may be involved in DNA damage recognition, but ERCC1 (in a complex with other proteins), may be primarily responsible for performing the excision function. This is consistent with what has been reported for ERCC1 in non-malignant human bone marrow specimens from 52 cancer patients (34), and in human ovarian cancer tissues (38). A recent report, using a cell-free system, suggests that XPA and ERCC1 form a protein complex, wherein ERCC1 has probable excision activity and XPA probably determines localization of the DNA damage and "loading" of the excision complex onto the damaged template (46). Our findings support this concept of possible interaction between the ERCC1 and XPA proteins.

REFERENCES

This application makes reference to several articles of the scientific literature. Each such article listed below is hereby incorporated in its entirety by reference.

1. J. E. Cleaver, Carcinogenesis 11:875–882 (1990).
2. J. H. J. Hoeijmakers et al., Cancer Cells 2:311–320 (1990).
3. M. K. K. Shivji et al., Cell 69:367–374 (1992).
4. A. Westerveld et al., Nature (London) 310:425–428 (1984).
5. K. Tanaka et al., Nature 348:73–76 (1990).
6. M. Dabholkar et al., J. Natl. Cancer Inst. 84:1512–1517 (1992).
7. F. J. Dijt et al., Cancer Res. 48:6058–6062 (1988).
8. J. Hansson et al., Nucleic Acids Res. 18: 35–40 (1990).
9. K. B. Lee et al., Carcinogenesis 14:2177–2180 (1993).
10. M. Bankmann et al., Nature 355:555–558 (1992).
11. A. E. Tomkinson et al., Nature 362:860–862 (1993).
12. Z. Wang et al., Proc. Natl. Acad. Sci. USA 90:4907–4911 (1993).
13. J. H. J. Hoeijmakers, J. Cell Science 100:687–691 (1991).
14. M. L. Rothenberg et al., J. Clin. Oncol. 10:727–734 (1992).
15. E. Reed et al., J. Clin. Oncol. 11:2118–2126 (1993).
16. M. L. Rothenberg et al., J. Natl. Cancer Inst. 80:1488–1492 (1988).
17. R. J. Parker et al., J. Clin. Invest. 87:772–777 (1991).
18. G. M. Wahl et al., J. Biol. Chem. 254:8679–8684 (1979).
19. M. van Duin et al., Cell 44:913–923 (1986).
20. J. H. J. Hoeijmakers et al., "Molecular genetic dissection of mammalian excision repair", in DNA Repair Mechanisms and Their Biological Implications in Mammalian Cells, M. W. Lambert, and J. Laval, editors. Plenum Publishers, New York. 563–574 (1989).
21. I. Satokata et al., Mutation Res. 273:203–212 (1992).
22. S. Nakajima-Iijima et al., Proc. Natl. Acad. Sci., USA 82:6133–6137 (1992).
23. T. Maniatis et al., Molecular Cloning—A Laboratory Manual, Second Edition, Volume 2. Cold Spring Harbour, N.Y. pp. 660 (1989).
24. M. Popovic et al., The Lancet 2(8417–18): 1472–1473 (1984).
25. E Reed, "Platinum analogs" in Cancer— Principles and Practice of Oncology, Fourth Edition. V. T. DeVita Jr., S. Hellman, and S. A. Rosenberg, editors. J. B. Lippincott Company, Philadelphia. 390–399 (1993).
26. M. Dabholkar et al., Mutation Res. 274:45–56 (1992).
27. A. Eastman et al., "Mechanisms of resistance to platinum drugs", in Platinum and Other Metal Coordination Compounds in Cancer Chemotherapy, Nicolini, M., editor. Martinus Nijhoff Publishing, Boston. 178–196 (1988).
28. N. Sheibani et al., Biochemistry 28:3120–3124 (1989).
29. R. D. Wood et al., Nature 348:13–14 (1990).
30. R. Geleziunas et al., J. Natl. Cancer Inst. 83:557–564 (1991).
31. I. Miyamoto et al., J. Biol. Chem. 267:12182–12187 (1992).
32. G. Chu and P. Berg., Mol. Biol. Med. 4:277–290 (1987).
33. E. H. Poll et al., Mutation Res. 132:181–187 (1984).
34. M. Dabholkar et al., Mutation Res. 293:151–160 (1993).
35. P. B. G. M. Belt et al., Nucleic Acids Res. 19:5633–5637 (1991).
36. A. Sancar, Science 266:1954 (1995).
37. C. H. Park and A. Sancar, Proc. Natl. Acad. Sci. USA 91:5017 (1994).
38. M. Dabholkar et al., J. Clin. Invest. 94:703 (1994)
39. M. van Duin et al., Nucl. Acids. Res. 15:9195 (1987).
40. B. L. Weber et al., Science 249:1291 (1990).
41. A. A. McBride et al., Proc. Natl. Acad. Sci. USA 86:510 (1989).
42. Y. Nakabeppu and D. Nathans, Cell 64:751 (1991).
43. M. van Duin et al., Nucleic Acids Res. 16:5305 (1988).
44. C. S. Downes, Nature 332:208 (1988).
45. J. H. H. Hoeijmakers, J. Cell Sci. Suppl 6:111 (1987).
46. L. Li et al., Proc. Natl. Acad. Sci. USA 91:5012 (1994).

What is claimed is:

1. A method for assaying sensitivity of ovarian tumor tissue to treatment with DNA platinating agents, comprising:
    i) measuring the amount of mRNA from said ovarian tumor tissue that encodes XPAC;
    ii) measuring the amount of mRNA from said ovarian tumor tissue that encodes ERCC1;
    iii) determining the ratio of XPAC mRNA measured in step (i) to the amount of ERCC1 mRNA measured in step (ii);
    iv) comparing the ratio of XPAC mRNA to ERCC1 mRNA measured in step (iii) with the ratio found in cells that are resistant to DNA platinating agents; and
    v) comparing the ratio of XPAC mRNA to ERCC1 mRNA measured in step (iii) with the ratio found in cells that are sensitive to DNA platinating agents;

wherein observing that the ratio of the amount of XPAC mRNA to the amount of ERCC1 mRNA is similar to that ratio in cells sensitive to DNA platinating agents and observing that said ratio of the amount of XPAC mRNA to the amount of ERCC1 mRNA is dissimilar to that ratio in cells resistant to DNA platinating agents results in an assessment that said ovarian tumor tissue is sensitive to treatment with DNA platinating agents.

2. The method of claim 1, wherein an assessment that said ovarian tumor tissue is sensitive to treatment with DNA platinating agents is obtained when the ratio of the amount of XPAC mRNA to the amount of ERCC1 mRNA is 0.17 or lower.

3. A method for assaying the sensitivity of ovarian tumor tissue to treatment with DNA platinating agents, comprising:
   i) measuring the amount of mRNA that encodes ERCC1 including exon VIII in said ovarian tumor tissue;
   ii) comparing the amount of mRNA that encodes ERCC1 including exon VIII in said ovarian tumor tissue to the amount of said mRNA found in cells that are sensitive to DNA platinating agents; and
   iii) comparing the amount of mRNA that encodes ERCC1 including exon VIII to the amount of said mRNA found in cells that are resistant to DNA platinating agents;

wherein observing that the amount of said mRNA in said ovarian tumor tissue is similar to the amount of said mRNA in cells sensitive to DNA platinating agents and observing that the amount of said mRNA is dissimilar to the amount in cells resistant to DNA platinating agents results in an assessment that said ovarian tumor tissue is sensitive to treatment with DNA platinating agents.

4. The method of claim 1, wherein the amount of said ERCC1 mRNA is measured using a polymerase chain reaction technique and a primer that hybridizes to a nucleotide sequence in ERCC1 exon VIII.

5. The method of claim 1, wherein the amount of said ERCC1 mRNA is measured by a polymerase chain reaction technique and a set of primers that flank the ERCC1 exon VIII, and further wherein the amount of ERCC1 mRNA equals the sum of the amounts of ERCC1 exon VIII⁺ and ERCC1 exon VIII⁻ mRNA.

6. The method of claim 1, wherein said ERCC1 mRNA is measured by a polymerase chain reaction technique and a set of primers that flank the ERCC1 exon VIII, and further wherein the amount of ERCC1 mRNA equals the amount of ERCC1 exon VIII⁺ mRNA.

7. The method of claim 1, wherein said ERCC1 mRNA is measured by a polymerase chain reaction technique and a set of primers that flank the ERCC1 exon VIII, and further wherein the amount of ERCC1 mRNA equals the amount of ERCC1 exon VIII⁻ mRNA.

8. The method of claim 4, wherein said primers have the sequence of SEQ. ID. NOS. 1 and 2.

9. The method of claim 5, wherein said primers have the sequence of SEQ. ID. NOS. 1 and 3.

10. The method of claim 6, wherein said primers have the sequence of SEQ. ID. NOS. 1 and 3.

11. A method for assaying the sensitivity of a T cell to treatment with DNA platinating agents, comprising:
   i) measuring the amount of mRNA that encodes ERCC1 lacking exon VIII in said T cell;
   ii) comparing the amount of mRNA that encodes ERCC1 lacking exon VIII in said T cell to the amount of said mRNA found in cells that are sensitive to DNA platinating agents; and
   iii) comparing the amount of mRNA that encodes ERCC1 lacking exon VIII in said T cell to the amount of said mRNA found in cells that are resistant to DNA platinating agents;

wherein observing that the amount of said mRNA in said T cell is similar to the amount of said mRNA in cells sensitive to DNA platinating agents and observing that the amount of said mRNA in said T cell is dissimilar to the amount in cells resistant to DNA platinating agents results in an assessment that said T cell is sensitive to treatment with DNA platinating agents.

12. The method of claim 11, wherein the amount of said ERCC1 mRNA lacking exon VIII is measured by a polymerase chain reaction technique and a set of primers that flank the ERCC1 exon VIII.

13. The method of claim 12, wherein said primers have the sequence of SEQ. ID. NOS. 1 and 3.

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="upstream synthetic primer"

( i i i ) HYPOTHETICAL: NO ( i v ) ANTI-SENSE: NO ( x i ) SEQUENCE DESCRIPTION: SEQ ID NO:1:

GAGCTGGCTA AGATGTGTAT CC        22

( 2 ) INFORMATION FOR SEQ ID NO:2:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="downstream synthetic
            primer, exon VIII+"

( i i i ) HYPOTHETICAL: NO ( i v ) ANTI-SENSE: YES ( x i ) SEQUENCE DESCRIPTION: SEQ ID NO:2:

AGGCCAGATC TTCTCTTGAT GC        22

( 2 ) INFORMATION FOR SEQ ID NO:3:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="downstream synthetic
            primer, total ERCC1 mRNA"

( i i i ) HYPOTHETICAL: NO ( i v ) ANTI-SENSE: YES ( x i ) SEQUENCE DESCRIPTION: SEQ ID NO:3:

TCATAGGCCT TGTAGGTCTC CAGGTA        26